US008859841B2

(12) United States Patent
Bissah et al.

(10) Patent No.: US 8,859,841 B2
(45) Date of Patent: *Oct. 14, 2014

(54) ABSORBENT ARTICLE INCLUDING AN ABSORBENT CORE LAYER HAVING A MATERIAL FREE ZONE AND A TRANSFER LAYER ARRANGED BELOW THE ABSORBENT CORE LAYER

(75) Inventors: Kofi Bissah, Somerset, NJ (US); John Poccia, Monmouth Beach, NJ (US); Fernanda Wiermann Paques, São Paulo (BR); Francisco J. V. Hernandez, São José dos Campos (BR)

(73) Assignee: McNeil-PPC, Inc., Skillman, NJ (US)

( * ) Notice: Subject to any disclaimer, the term of this patent is extended or adjusted under 35 U.S.C. 154(b) by 319 days.

This patent is subject to a terminal disclaimer.

(21) Appl. No.: 13/326,717

(22) Filed: Dec. 15, 2011

(65) Prior Publication Data

US 2012/0323201 A1 Dec. 20, 2012

Related U.S. Application Data

(63) Continuation-in-part of application No. 12/554,047, filed on Sep. 4, 2009.

(51) Int. Cl.
| *A61F 13/532* | (2006.01) |
| *A61F 13/537* | (2006.01) |
| *A61F 13/475* | (2006.01) |
| *A61F 13/533* | (2006.01) |
| *A61F 13/539* | (2006.01) |
| *A61F 13/53* | (2006.01) |

(52) U.S. Cl.
CPC ......... *A61F 13/533* (2013.01); *A61F 13/53756* (2013.01); *A61F 13/53717* (2013.01); *A61F 2013/530875* (2013.01); *A61F 13/4758* (2013.01); *A61F 13/5323* (2013.01); *A61F 13/4756* (2013.01); *A61F 13/539* (2013.01)
USPC .......................................................... 604/378

(58) Field of Classification Search
CPC ............ A61F 13/4756; A61F 13/5323; A61F 13/53756
USPC ......................................................... 604/378
See application file for complete search history.

(56) References Cited

U.S. PATENT DOCUMENTS

| 4,624,666 A | 11/1986 | DeRossett et al. |
| 4,840,692 A | 6/1989 | Kamstrup-Larsen |
| 4,973,325 A | 11/1990 | Sherrod et al. |
| 4,988,344 A * | 1/1991 | Reising et al. ................. 604/368 |
| 4,988,345 A * | 1/1991 | Reising ......................... 604/368 |

(Continued)

FOREIGN PATENT DOCUMENTS

| EP | 2055279 | 5/2009 |
| WO | WO 86/01378 | 3/1986 |

(Continued)

*Primary Examiner* — Susan Su

(57) ABSTRACT

An absorbent article including a liquid permeable cover layer, a liquid impermeable barrier layer, an absorbent core arranged adjacent to the cover layer, the absorbent core including a material-free zone extending, a transfer layer arranged between the core and the barrier layer, the transfer layer including a planar portion having an upper surface and a lower surface and a protrusion extending upwardly from the upper surface.

18 Claims, 11 Drawing Sheets

(56) References Cited

U.S. PATENT DOCUMENTS

| | | |
|---|---|---|
| 5,176,672 A | 1/1993 | Bruemmer et al. |
| 5,304,161 A | 4/1994 | Noel et al. |
| 5,505,720 A | 4/1996 | Walters et al. |
| 5,624,423 A | 4/1997 | Anjur et al. |
| 5,662,633 A | 9/1997 | Doak et al. |
| 5,810,798 A | 9/1998 | Finch et al. |
| 5,954,705 A | 9/1999 | Sawaki et al. |
| 6,245,962 B1 | 6/2001 | Muhs et al. |
| 6,984,225 B2 | 1/2006 | Raidel et al. |
| 7,122,023 B1 | 10/2006 | Hinoki |
| 7,429,689 B2 * | 9/2008 | Chen et al. .................. 604/378 |
| 2003/0045851 A1 | 3/2003 | Vartiainen |
| 2004/0176734 A1 | 9/2004 | Rasmussen et al. |
| 2004/0243078 A1 | 12/2004 | Guidotti et al. |
| 2004/0254554 A1 | 12/2004 | Mavinkurve et al. |
| 2005/0124953 A1 | 6/2005 | Woltman et al. |
| 2006/0069366 A1 | 3/2006 | Cole |
| 2009/0112173 A1 | 4/2009 | Bissah et al. |
| 2010/0256586 A1 | 10/2010 | Bergstrom et al. |
| 2011/0060303 A1 | 3/2011 | Bissah et al. |

FOREIGN PATENT DOCUMENTS

| | | |
|---|---|---|
| WO | WO 91/09582 | 7/1991 |
| WO | WO 95/17869 | 7/1995 |
| WO | WO 01/97736 | 12/2001 |
| WO | WO 2009067059 | 5/2009 |

* cited by examiner

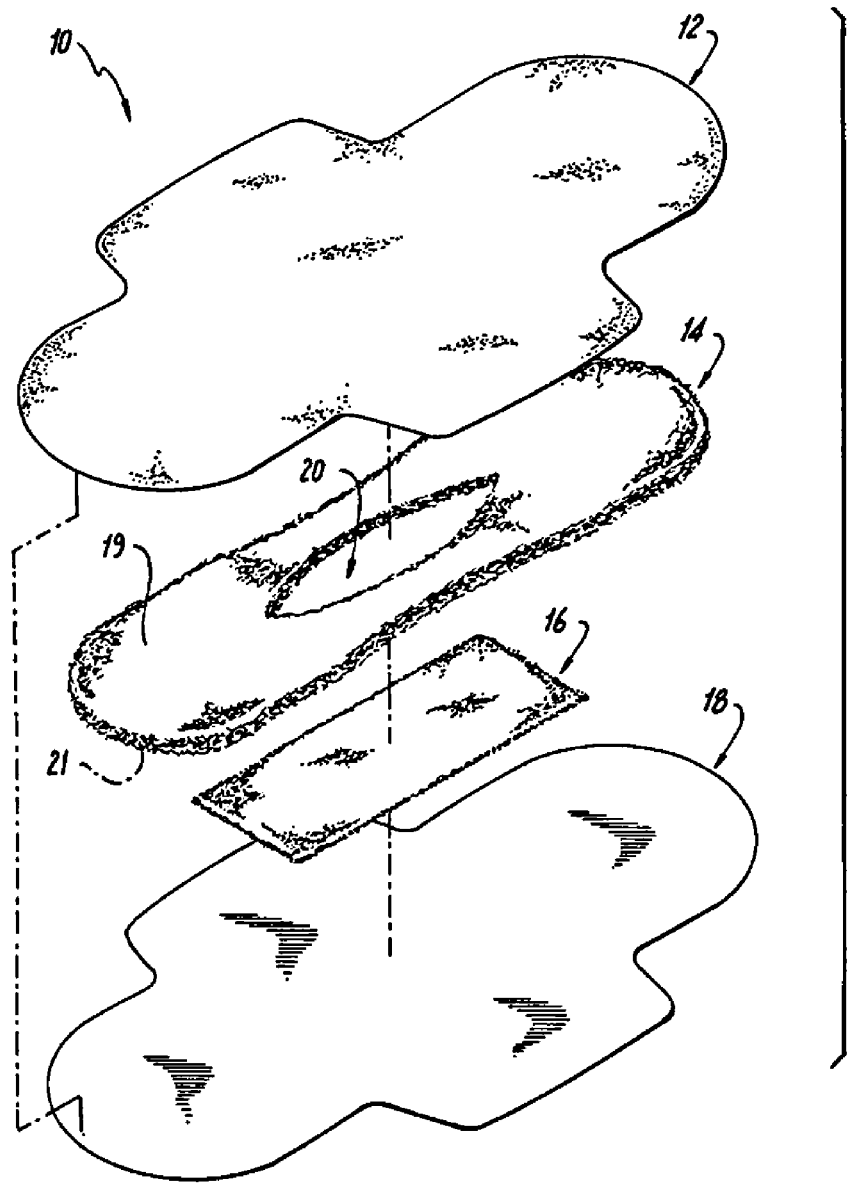
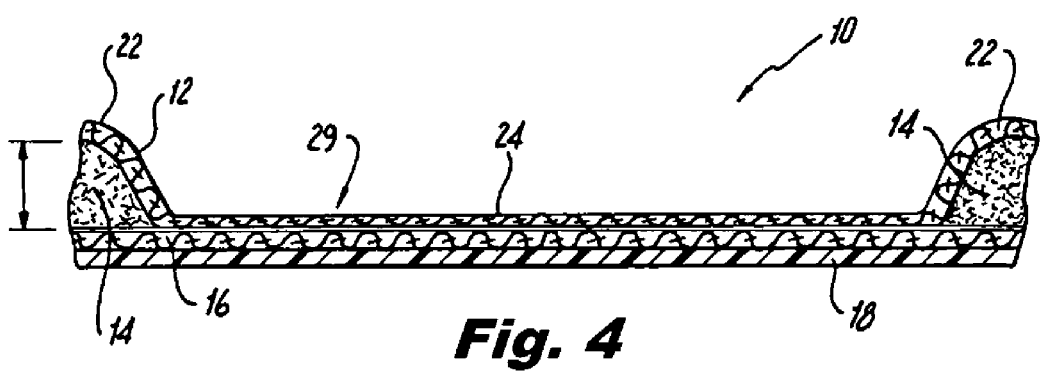

ABSORBENT ARTICLE INCLUDING AN ABSORBENT CORE LAYER HAVING A MATERIAL FREE ZONE AND A TRANSFER LAYER ARRANGED BELOW THE ABSORBENT CORE LAYER

CROSS-REFERENCE TO RELATED APPLICATION

The present application is a continuation-in-part application of U.S. patent application Ser. No. 12/554,047, filed on Sep. 4, 2009, priority of which is hereby claimed.

FIELD OF INVENTION

The present invention generally relates to absorbent sanitary napkins and in particular to a sanitary napkin that has superior transverse and longitudinal wicking characteristics, as well as superior fluid penetration time and rewet properties.

BACKGROUND OF THE INVENTION

In order for a sanitary napkin to efficiently absorb a large amount of fluid during use it must effectively wick fluid throughout the absorbent structure of the napkin. Absent effective wicking properties menstrual fluid tends to pool in certain regions of the napkin as a result of which the full absorbent capacity of the napkin is not effectively utilized. Accordingly, the inventors of the present invention have recognized a need to provide a sanitary napkin that efficiently wicks fluid in the longitudinal and transverse directions of the napkin to thereby fully utilize the full absorbent capacity of the napkin, while also providing superior fluid penetration time and rewet properties.

SUMMARY OF THE INVENTION

In view of the foregoing, the present invention provides, according to a first aspect of the invention, an absorbent article including a longitudinally extending centerline, a transversely extending centerline, a liquid permeable cover layer having a body facing surface, a liquid impermeable barrier layer, an absorbent core arranged adjacent to the cover layer, the absorbent core including an upper surface and a lower surface and a material-free zone extending from the upper surface to the lower surface, a transfer layer arranged between the core and the barrier layer, the transfer layer including a planar portion having an upper surface and a lower surface and a protrusion extending upwardly from the upper surface, wherein the cover layer includes a first region arranged in spaced relationship to the transfer layer and a second region arranged in surface to surface contact with the transfer layer, wherein the protrusion is structured and arranged to be received within, and extend upwardly into the material free zone, and wherein the protrusion has a height that is less than or equal to a distance between the upper surface of the absorbent core and the lower surface of the absorbent core.

The present invention provides, according to a second aspect of the invention, an absorbent article including a longitudinally extending centerline, a transversely extending centerline, a liquid permeable cover layer having a body facing surface, a liquid impermeable barrier layer, an absorbent core arranged adjacent to the cover layer, the transfer layer including a planar portion having an upper surface and a lower surface and a plurality of protrusion extending upwardly from the upper surface, wherein the absorbent core includes an upper surface and a lower surface, the absorbent core comprising a plurality of beams and a plurality of material-free zones, each of the beams arranged in a spaced relationship to an adjacent beam and each of the beams being separated from an adjacent beam by a material-free zone, each of the material-free zones extending from the upper surface to the lower surface, wherein the cover layer includes a plurality of first regions arranged in spaced relationship to the transfer layer and a plurality of second regions, each of the second regions located between two adjacent beams and arranged in surface to surface contact with the transfer layer, wherein each one of the plurality of protrusions is structured and arranged to be received within, and extend upwardly into one of the plurality of material free zones, and wherein each protrusion has a height that is less than or equal to a distance between the upper surface of the absorbent core and the lower surface of the absorbent core.

BRIEF DESCRIPTION OF THE DRAWINGS

Examples of embodiments of the present invention will now be described with reference to the drawings, in which:

FIG. 3 is an exploded view of the absorbent article shown in FIG. 1 according to a first embodiment of the invention;

FIG. 4 is sectional view of the absorbent article shown in FIG. 1 taken along line 4-4 in FIG. 1;

DETAILED DESCRIPTION OF THE INVENTION

Figure 1:
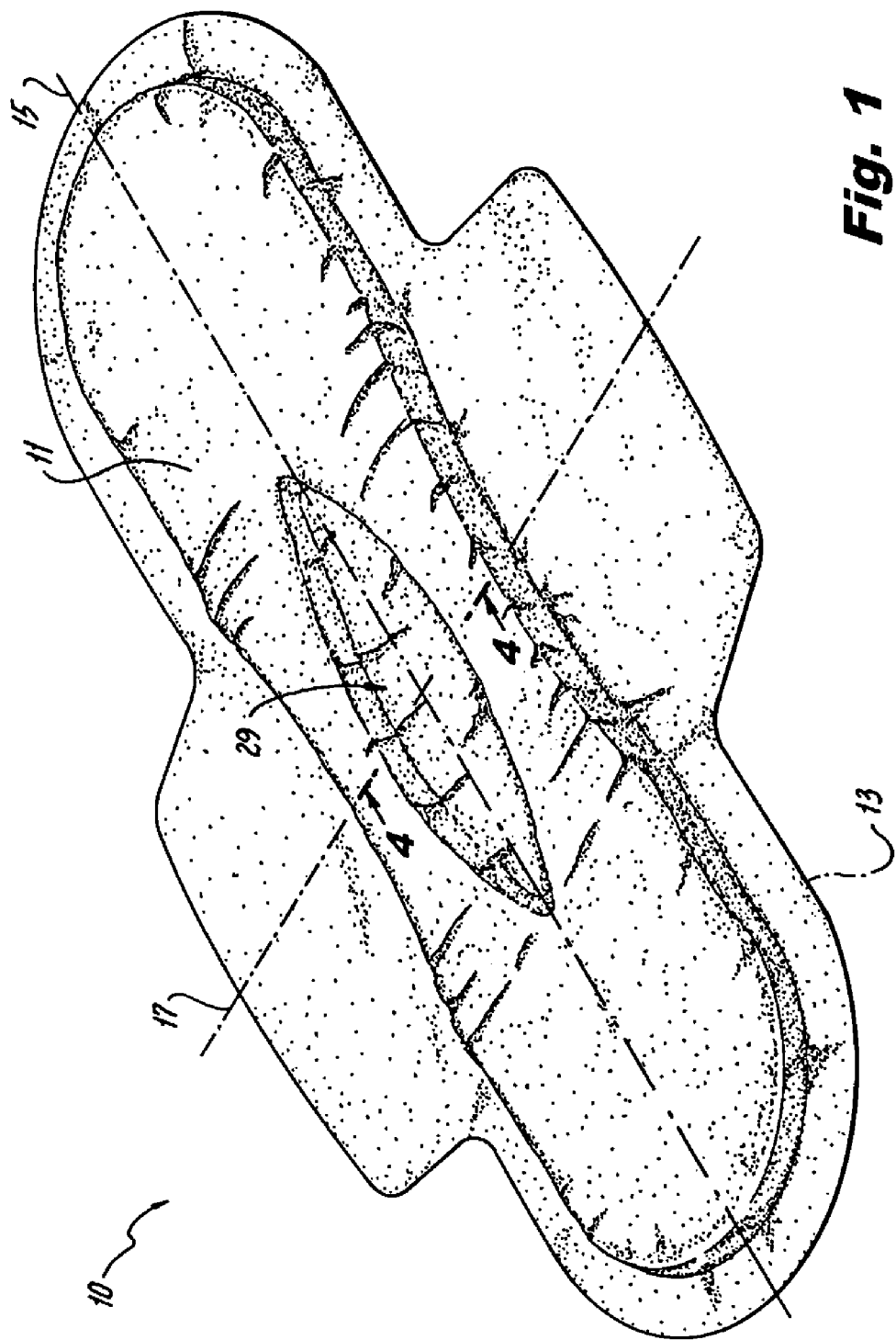
FIG. 1 is a top perspective view of an absorbent article according to the present invention.

The present invention generally relates to disposable absorbent articles such as sanitary napkins, pantiliners, absorbent products for incontinence, and other disposable absorbent articles worn close to a wearer's body. Although the invention will be described herein with reference to a sanitary napkin, the invention may be utilized with other disposable sanitary absorbent articles such as absorbent products for incontinence, diapers, pantiliners and the like.

Absorbent articles according to the present invention provide superior fluid handling characteristics, and more specifically provide superior longitudinal and transverse wicking characteristics, as well as superior fluid penetration time and rewet properties.

As shown in FIGS. 1-4, the present invention relates to a sanitary napkin 10 for absorbing bodily fluids. The sanitary napkin 10 includes a body facing surface 11, a garment facing surface 13, a longitudinally extending centerline 15, and a transversely extending centerline 17.

As best seen in the exploded view shown in FIG. 3, the sanitary napkin 10 includes a fluid permeable cover layer 12, an absorbent core 14, a transfer layer 16, and a fluid impermeable barrier layer 18. As shown in FIG. 3, the absorbent core 14 is arranged adjacent to the cover layer 12 and the transfer layer 16 is arranged between the absorbent core 14 and the barrier layer 18.

The absorbent core 14 includes a material-free zone 20 that is devoid of any absorbent material. The material-free zone 20 extends from an upper surface 19 of the absorbent core 14 to a lower surface 21 of the absorbent core 14. The material-free zone 20 may be formed by any known method such as cutting or the like. In the specific embodiment of the invention shown in FIGS. 1-4 the material-free zone 20 is centrally aligned with respect to the longitudinally extending centerline 15 and the transversely extending centerline 17. In the specific embodiment of the invention shown in FIGS. 1-4, the material-free zone 20 is substantially elliptical in shape and preferably has a length as measured along the longitudinally extending centerline 15 in the range of about 40 mm to about 160 mm and a width as measured along the transversely extending centerline 17 of about 10 mm to about 60 mm. The material-free zone 20 preferably extends over a surface area in the range of between 400 mm$^2$ and about 6000 mm$^2$.

As best seen in FIG. 4, the cover layer 12 includes a first region 22 located outside the area of the material-free zone 20 that is arranged in spaced relationship to the transfer layer 16 and the cover layer includes a second region 24 within the area defined by the material-free zone 20 that is arranged in surface to surface contact with the transfer layer 16. The surface to surface contact of the cover layer 12 with the transfer layer 16 essentially defines a gutter 29 in the body facing surface 11 of the napkin 10. The absorbent core 14 preferably has a thickness of between about 0.5 mm and about 20 mm. The depth of the gutter 29 is in the range of between about 0.5 mm and about 20 mm. The thickness and depth measurements set forth in this paragraph may be determined by using a suitable thickness gauge such as the Mitutoyo Absolute Gauge or equivalent.

Figure 5:
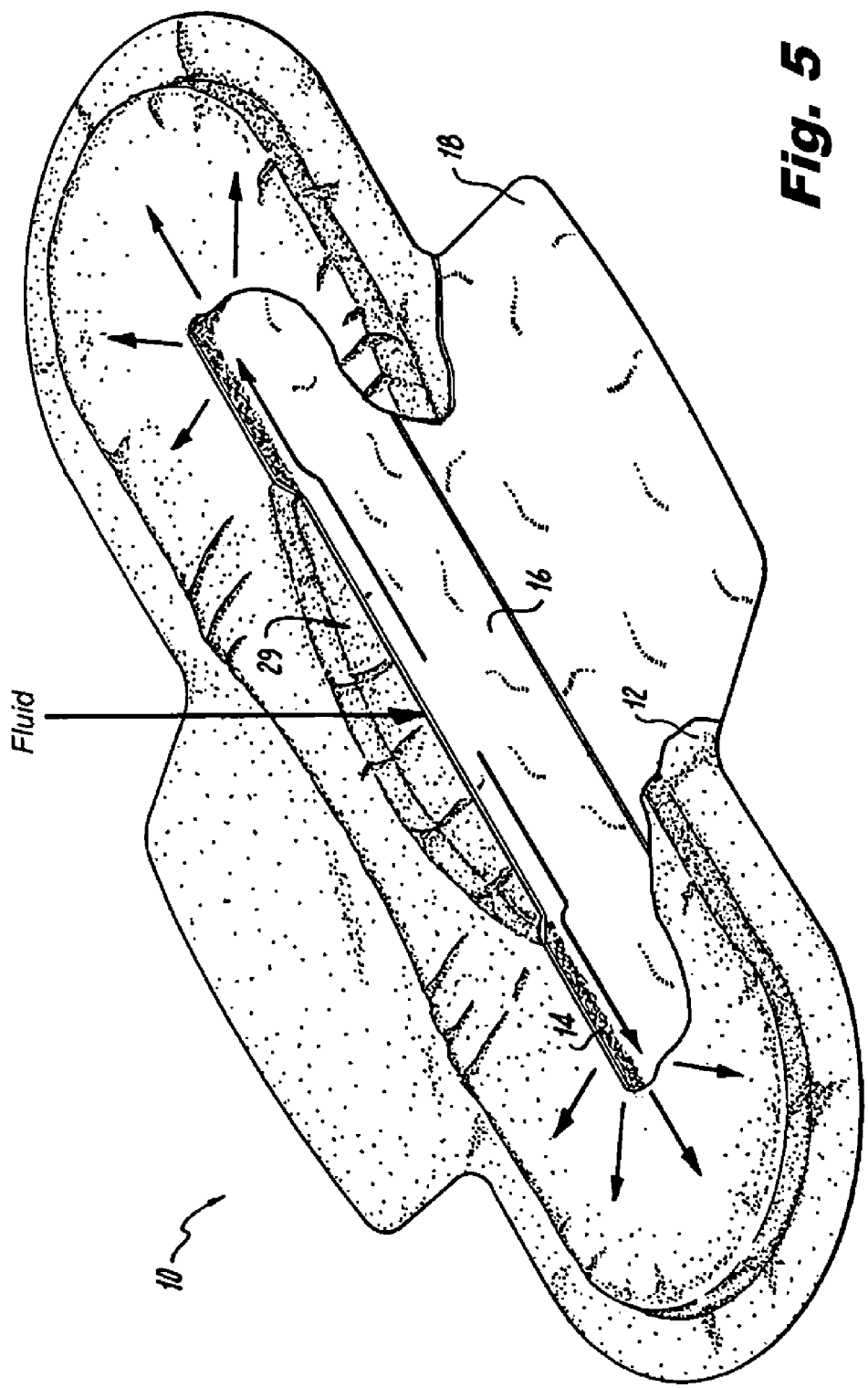
FIG. 5 is partially cut-away perspective view of the absorbent article shown in FIG. 1 schematically depicting the path of fluid flow within the article.

Reference is made to FIG. 5 which depicts the manner in which fluid is conveyed within the absorbent structure of a napkin 10 according to the present invention. As show, the transfer layer 16 directly receives fluid from the cover layer 12 in the area of the material-free zone 20. The transfer layer 16 then wicks the fluid in the longitudinal and transverse directions of the napkin until the fluid can be conveyed upward and absorbed into the absorbent core 14.

Figure 6:
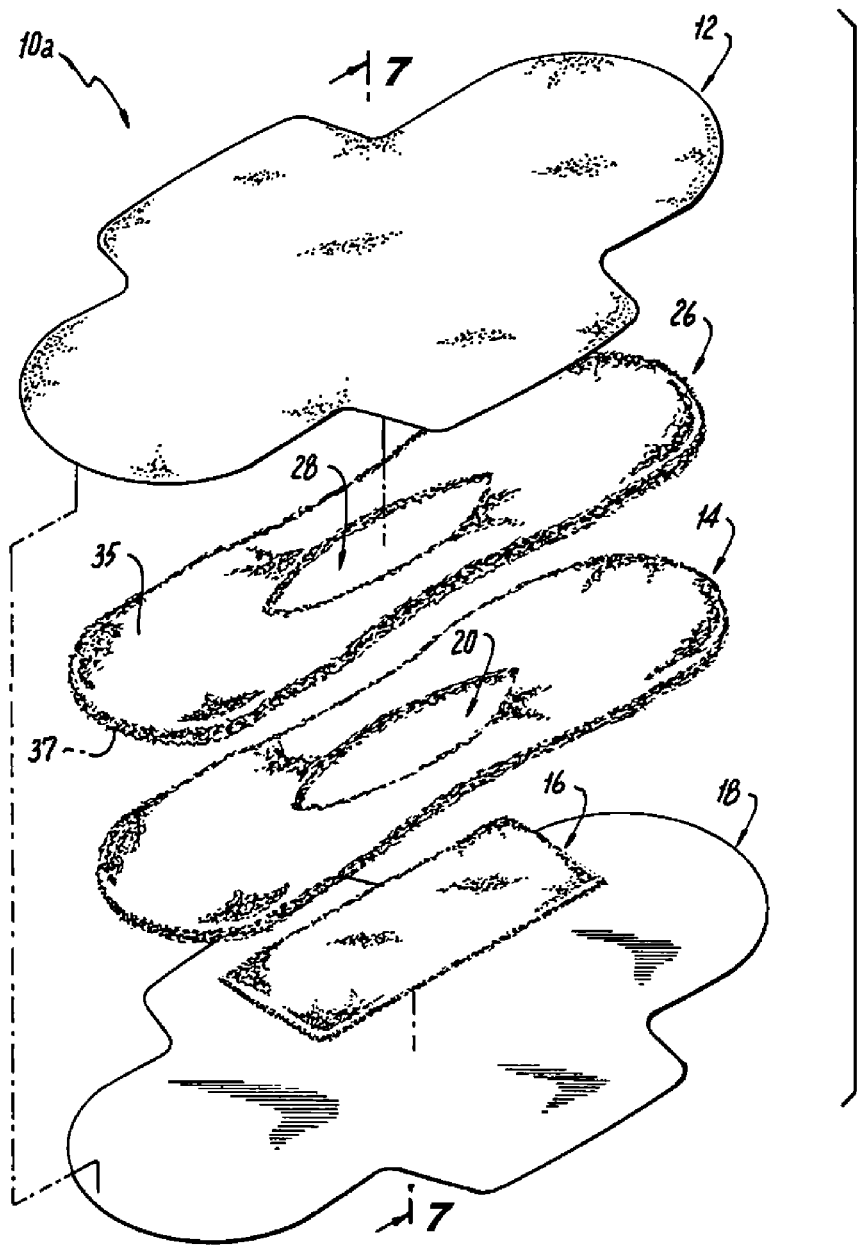
FIG. 6 is an exploded view of the absorbent article shown in FIG. 1 according to a second embodiment of the invention.

Reference is made to FIG. 6 which depicts an exploded view of a sanitary napkin 10a according to a second embodiment of the present invention. The sanitary napkin 10a is similar in structure to the sanitary napkin 10 described above but further includes a secondary absorbent core 26 arranged between the primary absorbent core 14 and the transfer layer 16. As shown, the secondary absorbent core 26 includes a material-free zone 28 that corresponds in size and shape to the material-free zone 20 of the primary absorbent core 14. The material-free zone 28 extends from an upper surface 35 of the secondary absorbent core 26 to a lower surface 37 of the secondary absorbent core 26.

Figure 7:
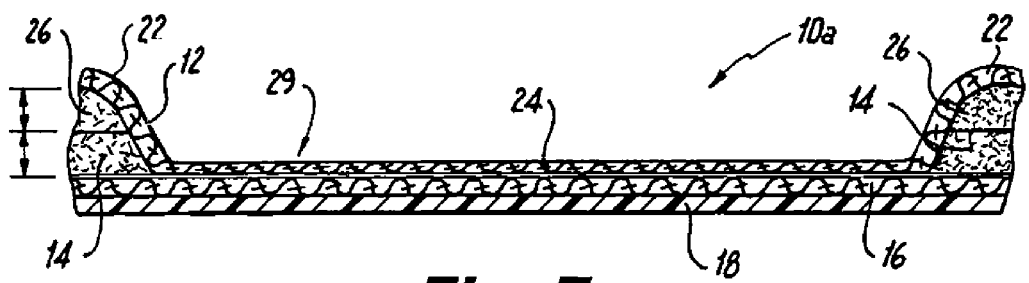
FIG. 7 is a sectional view of the absorbent article shown in FIG. 6 taken along line 7-7 in FIG. 6.

Referring to FIG. 7, the cover layer 12 includes a first region 22 located outside the area of the material-free zones 20 and 28 that is arranged in spaced relationship to the transfer layer 16 and the cover layer includes a second region 24 within area of the material-free zones 20 and 28 that is arranged in surface to surface contact with the transfer layer 16. The surface to surface contact of the cover layer 12 with the transfer layer 16 essentially defines a gutter 29 in the body facing surface of the napkin 10. The primary absorbent core 14 and the secondary absorbent core 28 preferably each has a thickness of between about 0.5 mm and about 20 mm. The depth of each gutter 29 is in the range of between about 1.0 mm and about 40 mm.

Figure 8:
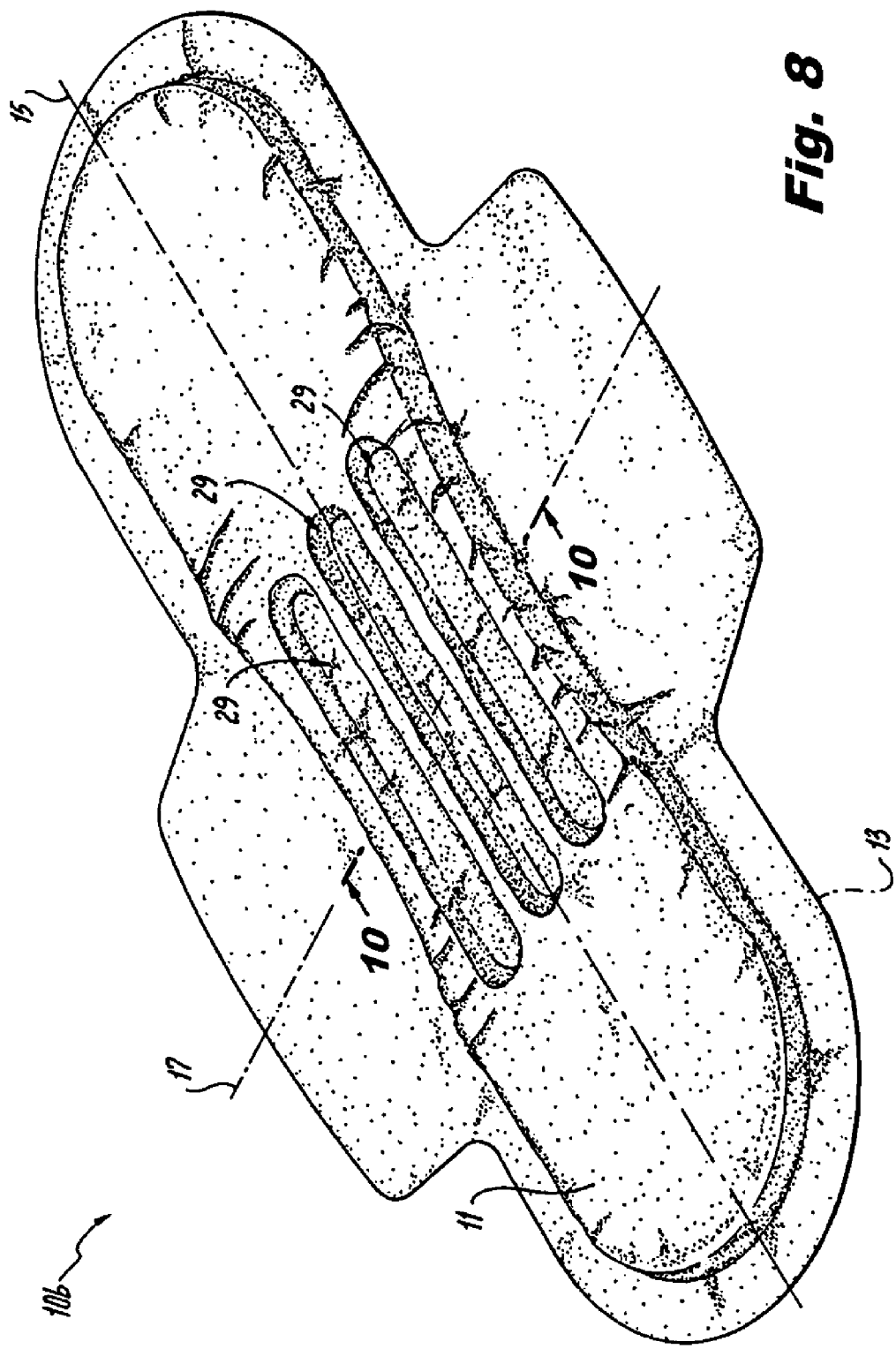
FIG. 8 is a top perspective view of an absorbent article according to a third embodiment of the present invention.
Figure 9:
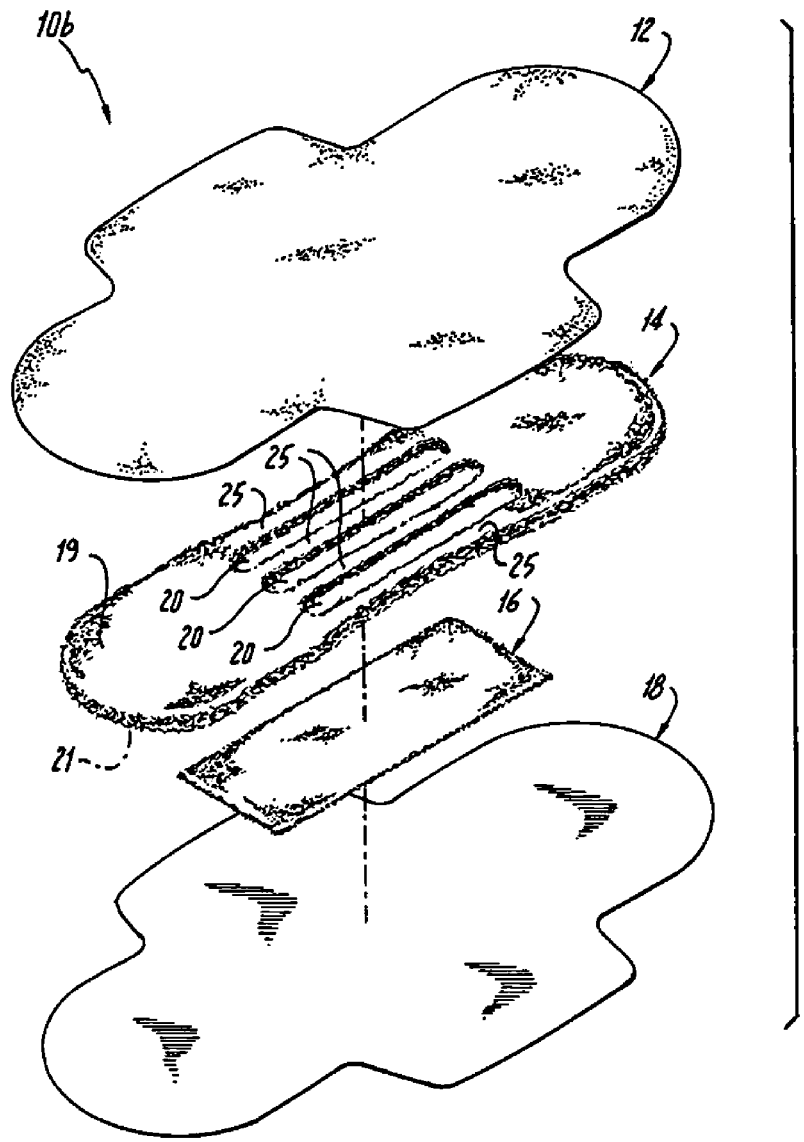
FIG. 9 is an exploded view of the absorbent article shown in FIG. 8.
Figure 10:
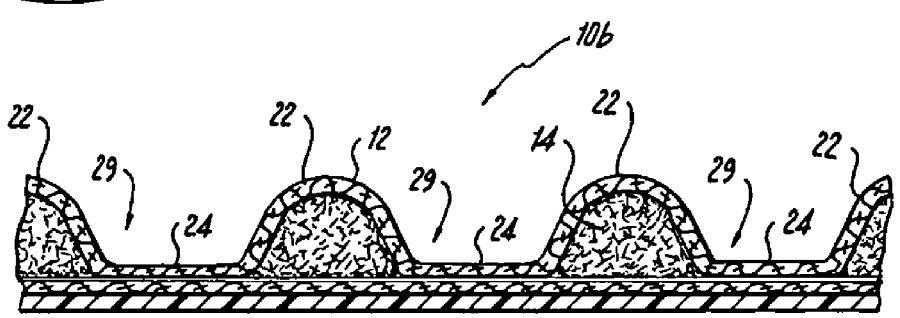
FIG. 10 is a sectional view taken of the absorbent article shown in FIG. 8 taken along line 10-10 in FIG. 8.

Reference is made to FIGS. 8-10 which depict a sanitary napkin 10b according to a third embodiment of the present invention. As shown in FIG. 9, the sanitary napkin 10b includes a fluid permeable cover layer 12, an absorbent core 14, a transfer layer 16, and a fluid impermeable barrier layer 18. As shown in FIG. 9, the absorbent core 14 is arranged adjacent to the cover layer 12 and the transfer layer 16 is arranged between the absorbent core 14 and the barrier layer 18.

As best seen in the exploded view shown in FIG. 9, the absorbent core 14 includes a plurality of longitudinally extending material-free zones 20 that extend from an upper surface 19 of the absorbent core 14 to a lower surface 21 of the absorbent core 14. Each of the material-free zones 20 preferably has a width in the range of between 1 mm and about 10 mm and a length in the range of between about 50 mm and about 250 mm. Absorbent articles according to the third embodiment of the present invention preferably have between about 2 and about 7 longitudinally extending the material-free zones 20. Each of the material free zones 20 is spaced from an adjacent material-free zone 20 in the transverse direction by a distance from about 5 mm to about 30 mm. Each of the material-free zones 20 preferably extends over a surface area in the range of between about 50 mm$^2$ and about 4000 mm$^2$. In the particular embodiment of the invention shown in the FIGS. 8-10 the material-free zones 20 are linear in shape, parallel to each other, and equally spaced.

The absorbent core 14 further includes a plurality of longitudinally extending beams 25, each of the beams 25 being arranged in spaced relationship to an adjacent beam 25 and each of the beams 25 being separated from an adjacent beam 25 by one of the material-free zones 20.

As best seen in FIG. 10, the cover layer 12 includes a plurality of first regions 22 that are arranged in spaced relationship to the transfer layer 16 and a plurality of second regions 24 that are arranged in surface to surface contact with the transfer layer 16. The surface to surface contact of the cover layer 12 with transfer layer 16 in the second regions 24 essentially define a plurality of longitudinally extending gutters 29 in the body facing surface 11 of the napkin 10 that are coextensive with the path of the material-free zones 20. The absorbent core 14 preferably has a thickness of between about 0.5 mm and about 20 mm. The depth of each gutter 29 is in the range of between about 0.5 mm and about 20 mm.

Although not shown in the Figures, the sanitary napkin 10b may be provided with a secondary absorbent core arranged between the primary core 14 and the transfer layer 16, the secondary absorbent core including a plurality of material-free zones that correspond in shape and size to the material-free zones of the primary core 14.

Although not shown in the Figures, the areas of the napkin in which the gutters 29 are located may be colored a different color than the remainder of the absorbent article. For example, the areas in which the gutters 29 are located may be colored blue while the remainder of the napkin is generally white. By coloring the gutters 29 a different color than the remainder of the napkin, the enhanced wicking characteristics provided by the gutters 29 are visually communicated to a potential user of the absorbent article. The color may be imparted to the napkin by providing a color (e.g., ink) to the cover layer 12 and/or the transfer layer 16 and/or the barrier layer 18.

Figure 11:
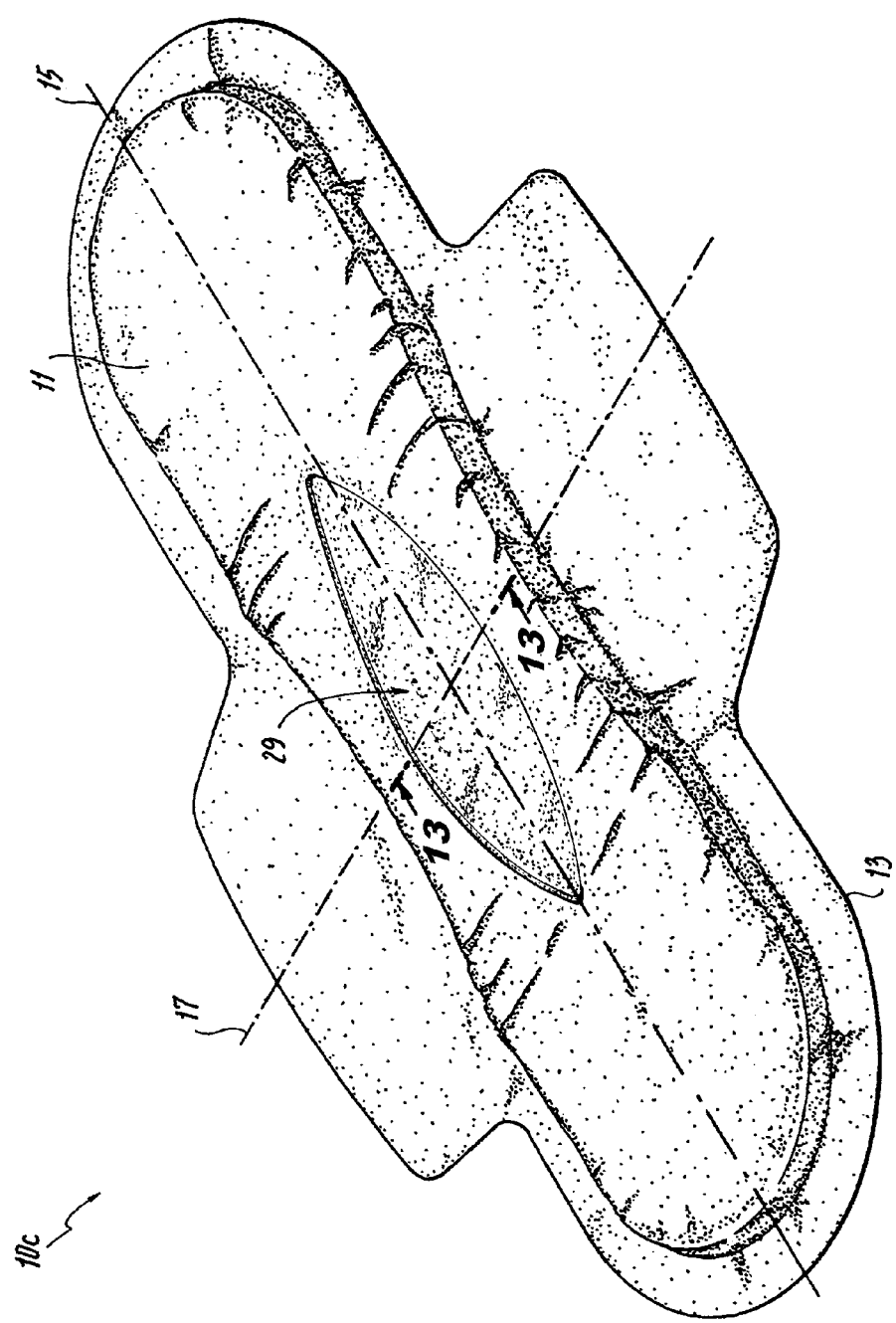
FIG. 11 is a top perspective view of an absorbent article according to a fourth embodiment of the present invention.
Figure 12:
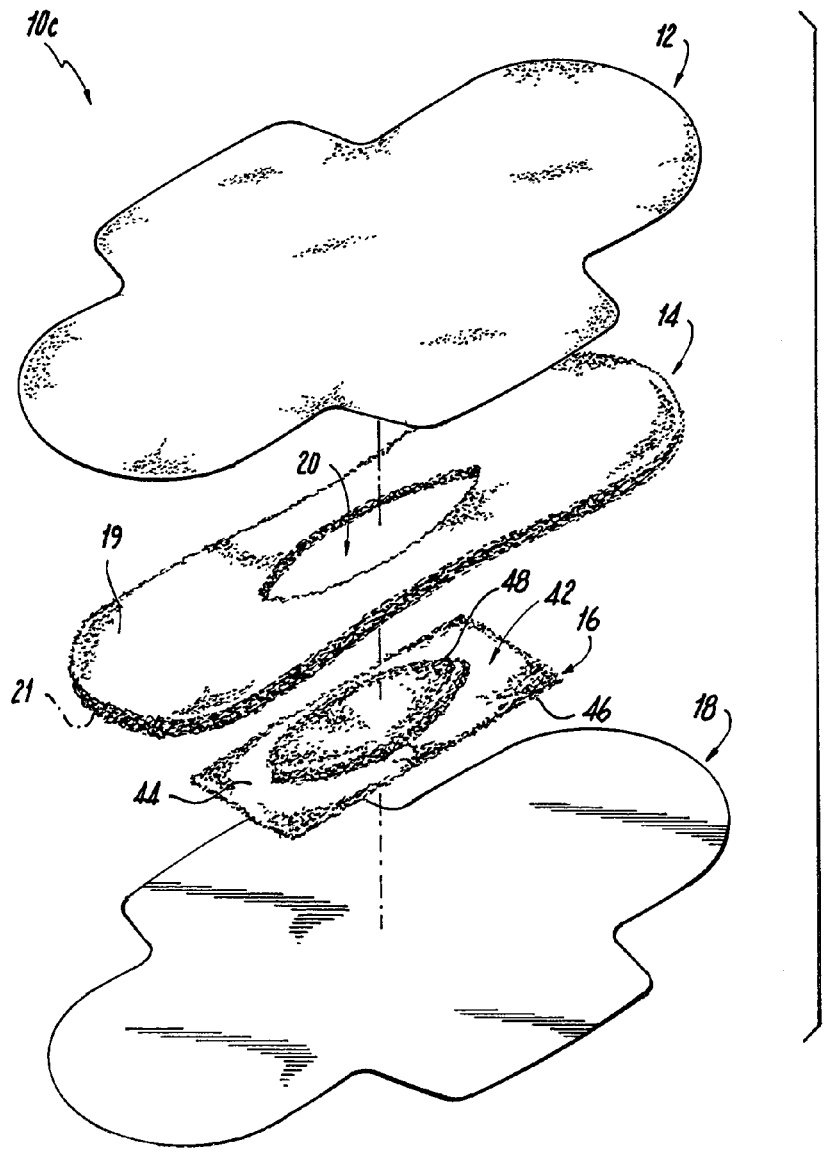
FIG. 12 is an exploded view of the absorbent article shown in FIG. 11.
Figure 13:
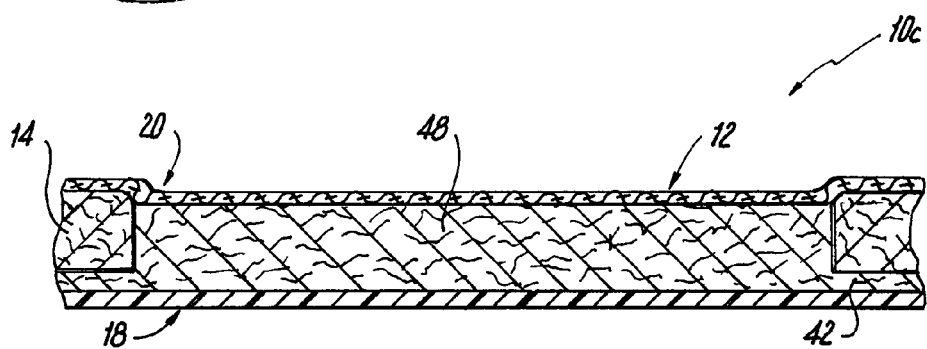
FIG. 13 is a sectional view of the absorbent article shown in FIG. 11 taken along line 13-13 in FIG. 11.

Reference is made to FIGS. 11-13 which depicts a sanitary napkin 10c according to a fourth embodiment of the present invention. The sanitary napkin 10c is similar in structure to the sanitary napkin 10 described above. However in the embodiment of the invention shown in FIGS. 11-13, the transfer layer 16 is provided with a planar portion 42 having an upper surface 44 and a lower surface 46 and a protrusion 48 that extends upwardly from the upper surface 44, as best seen in FIG. 12. In the specific embodiment of the invention shown in FIGS. 11-13, the protrusion 48 is structured and arranged to align with the material free zone 20 of the absorbent core 14. More specifically, as seen in FIG. 13, the protrusion 48 is structured and arranged to be received within, and extend upwardly into, the material free zone 20 of the absorbent core 14.

In the specific embodiment of the invention shown in FIGS. 11-13 the protrusion 48 is generally elliptical in shape and preferably has a length as measured along the longitudinally extending centerline in the range of about 40 mm to about 160 mm and a width as measured long the transversely extending centerline of about 10 mm to about 60 mm. The protrusion 48 preferably extends over a surface area in the range of between about 400 mm$^2$ to about 6000 mm$^2$.

The protrusion 48 preferably has a height that is less than or equal to the distance between the upper surface 19 of the absorbent core to the lower surface 21 of the absorbent core 14. Preferably the height of the protrusion 48 is in the range of between about 0.3 mm to about 20 mm, more preferably in the range of between about 0.4 mm and 19 mm and most preferably in the range of between about 0.5 mm and 18 mm. The term "height of the protrusion" as used herein means the distance the protrusion extends above the upper surface 44 of the planar portion 42. In the case where the protrusion 48 has a height that is less than the distance between the upper surface 19 of the absorbent core to the lower surface 21 of the absorbent core 14 the sanitary napkin 10c may include a gutter 29 in the body facing surface 11 of the napkin 10c, as shown in FIG. 11.

The planar portion 42 and the protrusion 48 of the transfer layer 16 may be formed by any conventional method known to those of skill in the art. For example, the transfer layer 16 may be compressed in area defining the planar portion 42 and non-compressed in the area defining the protrusion 48.

Figure 14:
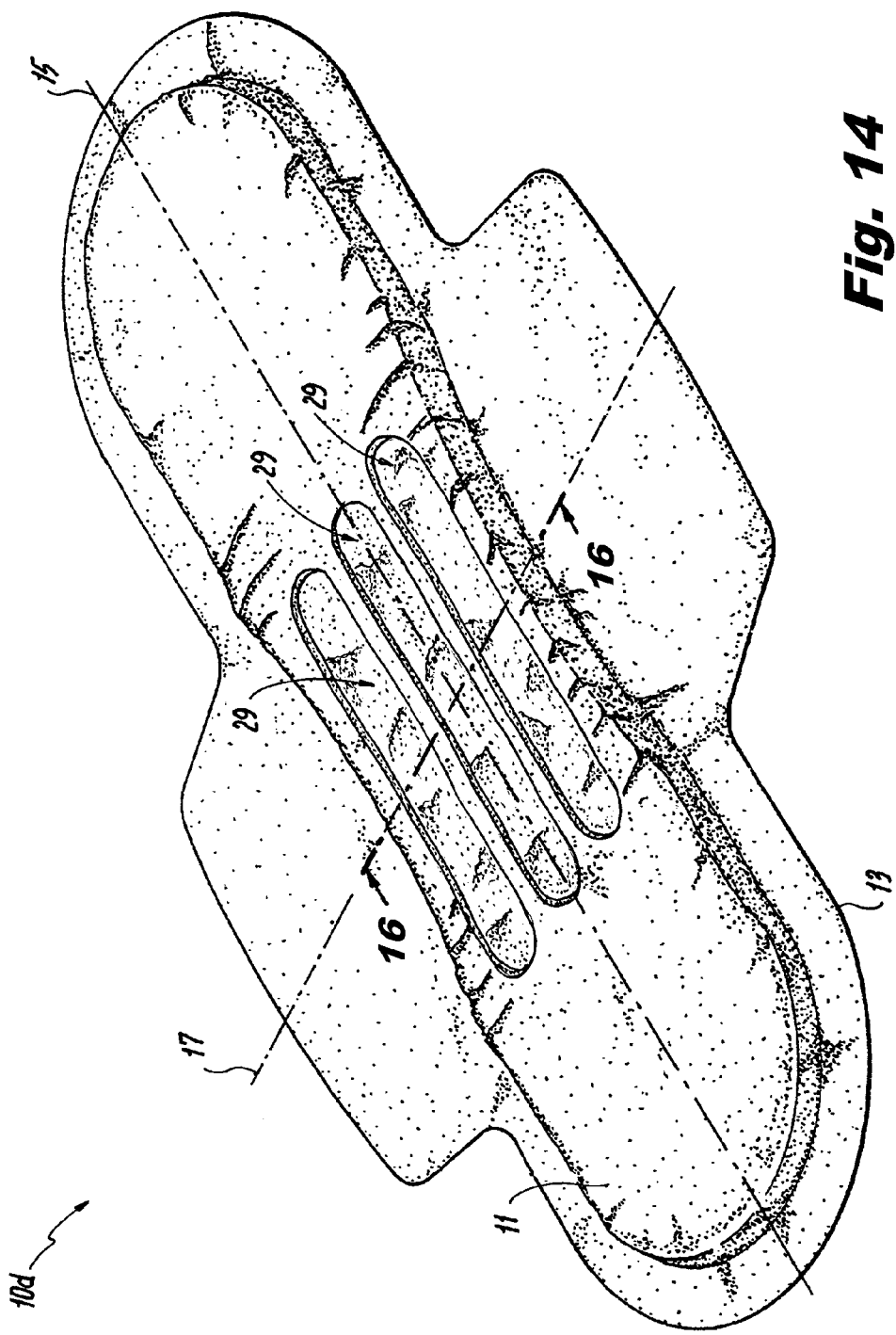
FIG. 14 is a top perspective view of an absorbent article according to a fifth embodiment of the present invention.
Figure 15:
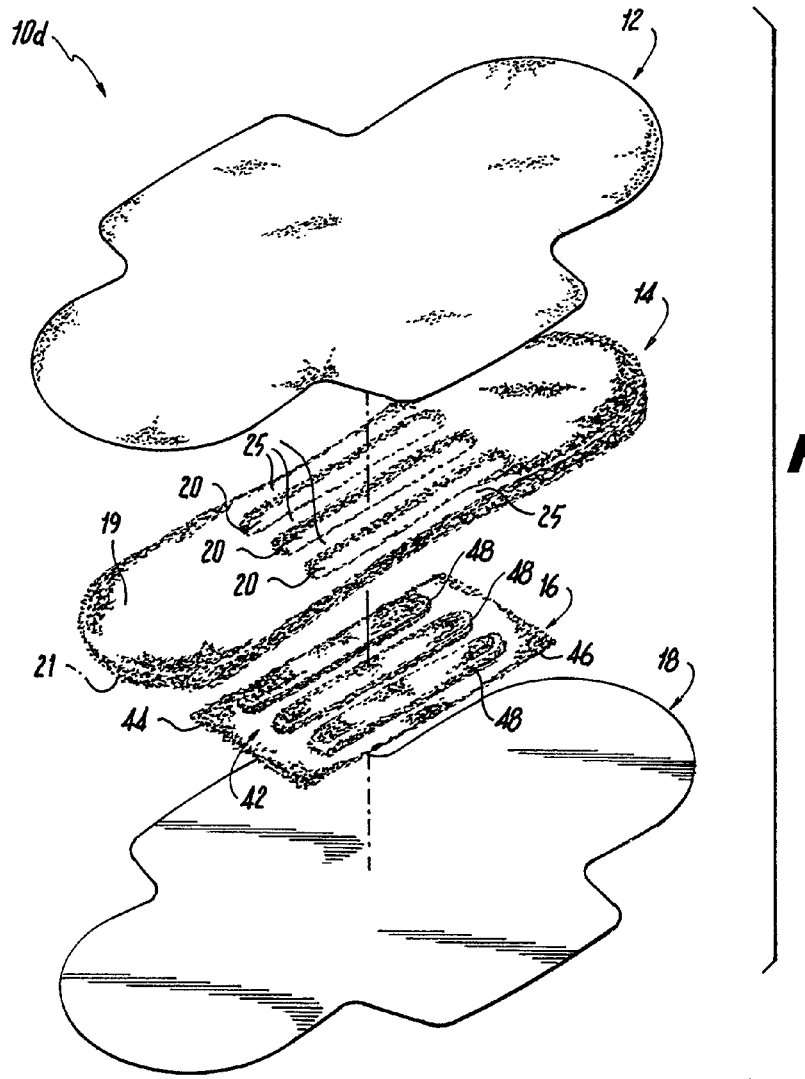
FIG. 15 is an exploded view of the absorbent article shown in FIG. 14.
Figure 16:
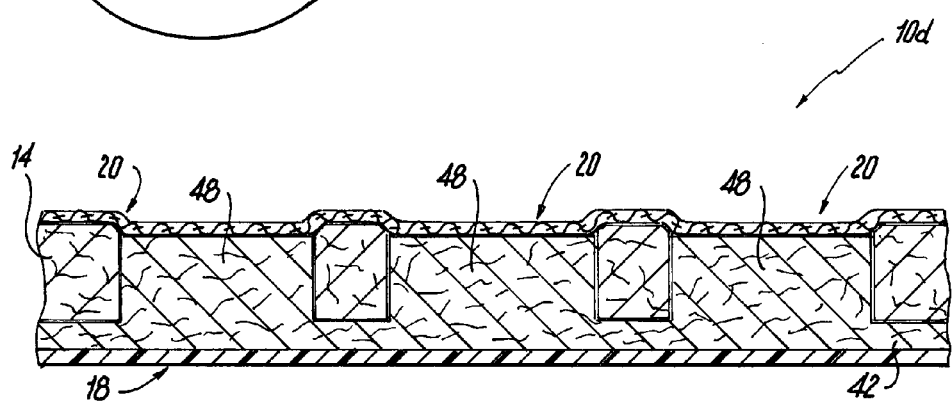
FIG. 16 is a sectional view of the absorbent article shown in FIG. 15 taken along line 16-16 in FIG. 14.

Reference is made to FIGS. 14-16 which depicts a sanitary napkin 10d according to a fifth embodiment of the present invention. The sanitary napkin 10d is similar in structure to the sanitary napkin 10b described above. However in the embodiment of the invention shown in FIGS. 14-16, the transfer layer 16 is provided with a planar portion 42 having an upper surface 44 and a lower surface 46 and a plurality of protrusions 48 that extend upwardly from the upper surface 44. In the specific embodiment of the invention shown in FIGS. 14-16, each of the protrusions 48 is structured and arranged to be aligned with one of the plurality of material free zones 20 in the absorbent core 14. More specifically, as seen in FIG. 16, each protrusion 48 is structured and arranged to be received within, and extend upwardly into, one of the material free zones 20 of the absorbent core 14.

In the specific embodiment of the invention shown in FIGS. 14-16 each protrusion 48 has a width in the range of between about 1 mm and about 10 mm and a length in the range of between about 50 mm and 250 mm. Absorbent articles according to this embodiment of the invention preferably have between about 2 and about 7 longitudinally extending protrusions 48. Each protrusion 48 is spaced from an adjacent protrusion by a distance from about 5 mm to about 30 mm. Each protrusion preferably extends over a surface area in the range of between about 50 mm$^2$ to about 4000 mm$^2$. In the particular embodiment of the invention shown in FIGS. 14-16 the protrusions 48 are linear in shape, parallel to each other, and equally spaced.

Preferably each protrusion 48 has a height that is less than or equal to the distance between the upper surface 19 of the absorbent core to the lower surface 21 of the absorbent core. Preferably the height of each protrusion 48 is in the range of between about 0.3 mm to about 20 mm, more preferably in the range of between about 0.4 mm and 19 mm and most preferably in the range of between about 0.5 mm and 18 mm. The term "height of the protrusion" as used herein means the distance the protrusion extends above the upper surface 44 of the planar portion 42. In the case where each protrusion 48 has a height that is less than the distance between the upper surface 19 of the absorbent core to the lower surface 21 of the absorbent core 14 the sanitary napkin 10d may include a plurality of gutters 29 in the body facing surface 11 of the napkin 10d, as shown in FIG. 14.

The planar portion 42 and each of the protrusions 48 may be formed by any conventional method known to those of skill in the art. For example, the transfer layer 16 may be compressed in area defining the planar portion 42 and non-compressed in the areas defining the protrusions 48.

Cover Layer

The cover layer 12 may be a relatively low density, bulky, high-loft non-woven web material. The cover layer 12 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 12 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layers of the article and/or to the barrier layer.

The cover layer 12 preferably has a relatively high degree of wettability, although the individual fibers comprising the cover may not be particularly hydrophilic. The cover material should also contain a great number of relatively large pores. This is because the cover layer 12 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 12 should not lose their physical properties when they are wetted, in other words they should not collapse or lose their resiliency when subjected to water or body fluid. The cover layer 12 may be treated to allow fluid to pass through it readily. The cover layer 12 also functions to transfer the fluid quickly to the underlying layers of the napkin. Thus, the cover layer 12 is advantageously wettable, hydrophilic and porous. When composed of synthetic hydrophobic fibers such as polyester or bi-component fibers, the cover layer 12 may be treated with a surfactant to impart the desired degree of wettability.

Alternatively, the cover layer 12 can be made of a polymer film having large pores. Because of such high porosity, the film accomplishes the function of quickly transferring body fluid to the underlying absorbent layers.

The cover layer 12 may be attached to the underlying absorbent core 14, transfer layer 16, and/or the barrier layer 18, by adhesion and/or other suitable means know to those of skill in the art.

Absorbent Core

In one embodiment, the absorbent core 14 is a blend or mixture of cellulosic fibers and superabsorbent disposed therein. Cellulosic fibers that can be used in the absorbent core 14 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The absorbent core 14 can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. of Osaka, Japan, under the designation of SA70N and products offered by Stockhausen Inc. In a specific example, the absorbent core is a material containing from 95% to about 40% percent cellulosic fiber by weight, and about 5% to about 60% SAP by weight.

In one specific embodiment of the invention, the absorbent core 14 is constructed from a mixture of fluff pulp, commercially available as RAYFLOC J-LD-E from Rayonier Products, Jessup, Ga., and superabsorbent polymer commercially available under the designation SA70N from Sumitomo Seika Chemicals Co., Ltd. Of Osaka, Japan, the mixture including 94% fluff pulp by weight and 6% superabsorbent polymer by weight.

Materials particularly suitable for use as the absorbent core preferably have a basis weight in the range from about 300 gsm (g/m$^2$) to 1000 gsm, $^a$ thickness in the range of about 0.5 mm to 20 mm, and a density in the range of about 0.015 g/cc to 2 g/cc.

Transfer Layer

Adjacent to the barrier layer 18 layer on its inner side is the transfer layer 16. The transfer provides the means of receiving body fluid from the cover layer 12 and holding it until the absorbent core 14 has an opportunity to absorb the fluid, and therefore serves as a fluid transfer or acquisition layer. In addition the transfer layer 16 functions to wick the fluid in the longitudinal and transverse directions of the napkin so that the full absorbent capacity of the napkin is utilized.

The transfer layer 16 is, preferably, has a larger proportion of smaller pores than the cover layer 12. These attributes allow the transfer layer 16 to contain body fluid and hold it away from the outer side of the cover layer 12, thereby preventing the fluid from re-wetting the cover layer 12 and its surface.

The transfer layer 16 may be composed of fibrous materials, such as wood pulp, polyester, rayon, flexible foam, or the like, or combinations thereof. Preferably, the transfer layer 16 is free of any superabsorbent polymer (SAP). The transfer layer 16 may also comprise thermoplastic fibers for the purpose of stabilizing the layer and maintaining its structural integrity. The transfer layer 16 may be treated with surfactant on one or both sides in order to increase its wettability, although generally the transfer layer 16 is relatively hydrophilic and may not require treatment. The transfer layer 16 is preferably bonded on both sides to the adjacent layers, i.e. the absorbent core 14 and the barrier layer 18.

Barrier Layer

Underlying the transfer layer 16 is a barrier layer 18 comprising liquid-impervious film material so as to prevent liquid from egressing the sanitary napkin and staining the wearer's undergarment. The barrier layer 18 is preferably made of polymeric film, although it may be made of liquid impervious, air-permeable material such as repellent-treated nonwoven or micropore films or foams.

The barrier layer 18 may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 12 and the barrier layer 18 are preferably joined along their marginal portions so as to form an enclosure or flange seal that maintains the transfer layer 16 and absorbent core 14 captive. The joint may be made by means of adhesives, heat-bonding, ultrasonic bonding, radio frequency sealing, mechanical crimping, and the like and combinations thereof.

Figure 2:
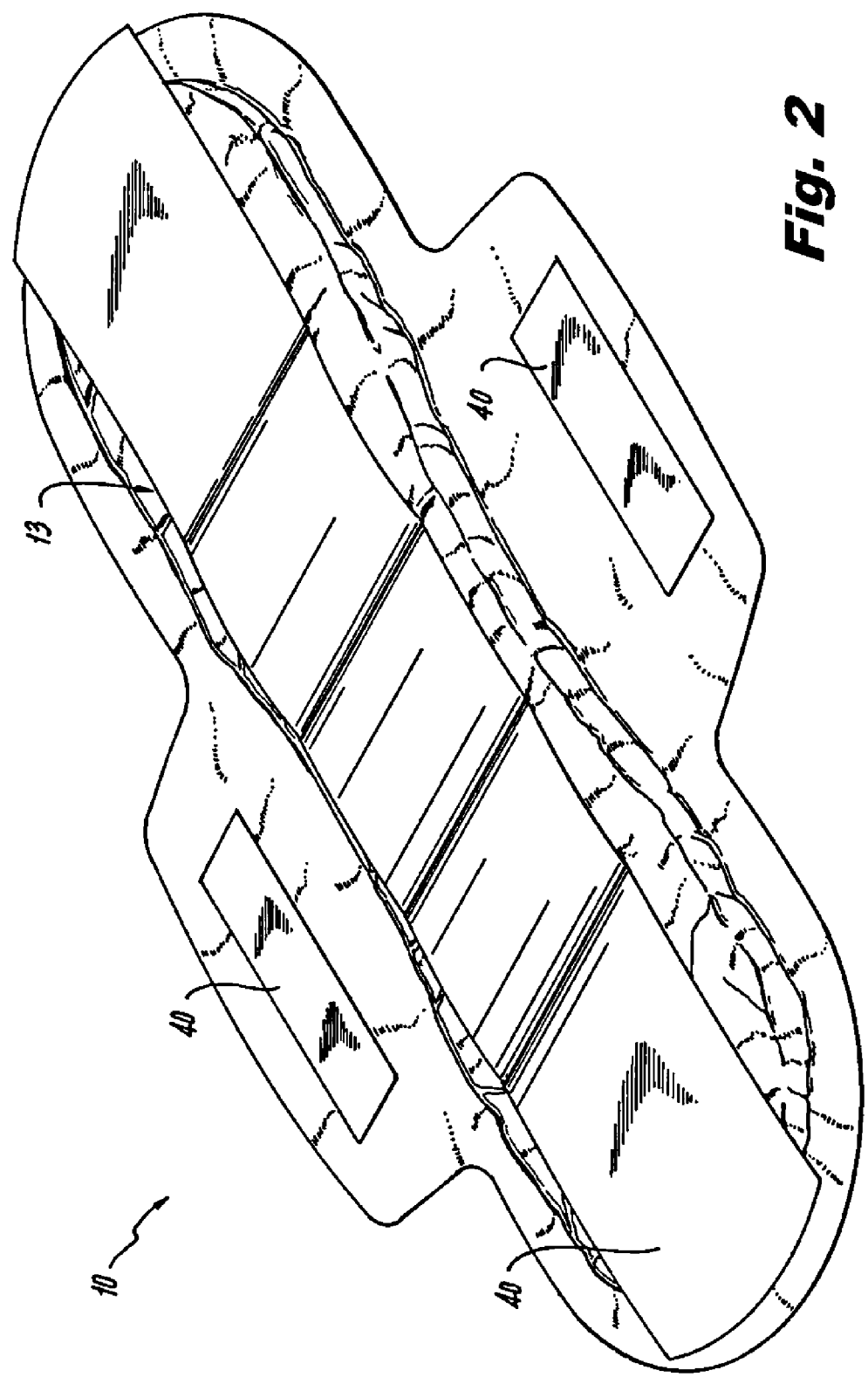
FIG. 2 is a bottom perspective view of the absorbent article shown in FIG. 1.

Positioning adhesive may be applied to a garment facing surface 13 of the barrier layer 18 for securing the napkin 10 to a garment during use. As seen in FIG. 2, the positioning adhesive may be covered with removable release paper 40 so that the positioning adhesive is covered by the removable release paper 40 prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

We claim:

1. An absorbent article comprising:
a longitudinally extending centerline;
a transversely extending centerline;
a liquid permeable cover layer having a body facing surface;
a liquid impermeable barrier layer;
an absorbent core arranged adjacent to the cover layer, the absorbent core including an upper surface and a lower surface and a material-free zone extending from the upper surface to the lower surface;
a transfer layer arranged between the core and the barrier layer, the transfer layer including a planar portion having an upper surface and a lower surface and a protrusion extending upwardly from the upper surface;
wherein the cover layer includes a first region arranged in spaced relationship to the transfer layer and a second region arranged in surface to surface contact with the transfer layer;
wherein the protrusion is structured and arranged to be received within, and extend upwardly into the material free zone; and
wherein the protrusion has a height that is less than a distance between the upper surface of the absorbent core and the lower surface of the absorbent core.

2. The absorbent article according to claim 1, wherein the material-free zone is centrally aligned with respect to the longitudinally extending centerline and the transversely extending centerline.

3. The absorbent article according to claim 2, wherein the material-free zone extends over an area between about 400 mm2 and about 6000 mm2.

4. The absorbent article according to claim 3, wherein the material-free zone is substantially elliptical in shape and preferably has a length as measured along the longitudinally extending centerline in the range of about 40 mm to about 250 mm and a width as measured along the transversely extending centerline of about 10 mm to about 60 mm.

5. The absorbent article according to claim 3, wherein the protrusion extends over an area between about 400 mm2 and about 6000 mm2.

6. The absorbent article according to claim 5, wherein the protrusion has a height in the range of between about 0.3 mm to about 20 mm.

7. The absorbent article according to claim 5, wherein the protrusion has a height in the range of between about 0.4 mm to about 19 mm.

8. The absorbent article according to claim 5, wherein the protrusion has a height in the range of between about 0.5 mm to about 18 mm.

9. An absorbent article comprising:
a longitudinally extending centerline;
a transversely extending centerline;
a liquid permeable cover layer having a body facing surface;
a liquid impermeable barrier layer;
an absorbent core arranged adjacent to the cover layer;
the transfer layer including a planar portion having an upper surface and a lower surface and a plurality of protrusion extending upwardly from the upper surface;
wherein the absorbent core includes an upper surface and a lower surface, the absorbent core comprising a plurality of beams and a plurality of material-free zones, each of the beams arranged in a spaced relationship to an adjacent beam and each of the beams being separated from an adjacent beam by a material-free zone, each of the material-free zones extending from the upper surface to the lower surface;
wherein the cover layer includes a plurality of first regions arranged in spaced relationship to the transfer layer and a plurality of second regions, each of the second regions located between two adjacent beams and arranged in surface to surface contact with the transfer layer;
wherein each one of the plurality of protrusions is structured and arranged to be received within, and extend upwardly into one of the plurality of material free zones; and
wherein each protrusion has a height that is less than a distance between the upper surface of the absorbent core and the lower surface of the absorbent core.

10. The absorbent article according to claim 9, wherein each of the material-free zones preferably has a width in the range of between about 1 mm and about 10 mm and a length in the range of between about 40 mm and about 250 mm.

11. The absorbent article according to claim 10, wherein the absorbent article includes between 2 and about 7 longitudinally extending material-free zones and each of the material free zones is spaced from an adjacent material-free zone in the transverse direction by a distance from about 5 mm to about 30 mm.

12. The absorbent article according to claim 11, wherein each of the material-free zones extend over a surface area in the range of between 50 mm2 and about 4000 mm2.

13. The absorbent article according to claim 12, wherein each protrusion has a width in the range of between about 1 mm and about 10 mm and a length in the range of between about 40 mm and about 250 mm.

14. The absorbent article according to claim 13, wherein the absorbent article includes between 2 and about 7 protrusions and each protrusion is spaced from an adjacent protrusion in the transverse direction by a distance from about 5 mm to about 30 mm.

15. The absorbent article according to claim 14, wherein each of the protrusions extend over a surface area in the range of between 50 mm2 and about 4000 mm2.

16. The absorbent article according to claim 15, wherein the protrusion has a height in the range of between about 0.3 mm to about 20 mm.

17. The absorbent article according to claim 16, wherein the protrusion has a height in the range of between about 0.4 mm to about 19 mm.

18. The absorbent article according to claim 17, wherein the protrusion has a height in the range of between about 0.5 mm to about 18 mm.

* * * * *